United States Patent [19]

Cragoe, Jr. et al.

[11] Patent Number: 4,771,076

[45] Date of Patent: Sep. 13, 1988

[54] [(2-SUBSTITUTED 1,2-DIHYDRO-1-OXO-1H-INDEN-5-YL)OXY-]ALKANESULFONIC ACIDS AND SALTS THEREOF

[75] Inventors: Edward J. Cragoe, Jr., Lansdale; Adolph M. Pietruszkiewicz, North Wales, both of Pa.

[73] Assignee: Merck & Co., Inc., Rahway, N.J.

[21] Appl. No.: 56,174

[22] Filed: Jun. 1, 1987

[51] Int. Cl.$^4$ .................... A61K 31/12; C07C 143/24
[52] U.S. Cl. ...................................... 514/577; 260/511
[58] Field of Search ......................... 514/577; 260/511

[56] References Cited

U.S. PATENT DOCUMENTS

| | | | |
|---|---|---|---|
| 3,250,804 | 5/1966 | Cragoe | 260/511 |
| 3,981,911 | 9/1976 | Sletzinger | 260/520 |
| 4,012,524 | 3/1977 | Cragoe | 424/308 |
| 4,051,260 | 9/1977 | Nelson et al. | 260/511 |
| 4,070,539 | 1/1978 | Cragoe | 560/56 |
| 4,096,267 | 6/1978 | Cragoe | 424/262 |
| 4,247,715 | 1/1981 | Johnson | 562/462 |
| 4,249,021 | 2/1981 | Cragoe | 562/462 |
| 4,291,050 | 9/1981 | Woltersdorf | 424/278 |
| 4,316,043 | 2/1982 | Cragoe | 560/53 |
| 4,317,922 | 3/1982 | Cragoe | 562/461 |
| 4,334,088 | 6/1982 | Johnson | 562/462 |
| 4,337,354 | 6/1982 | Cragoe | 562/461 |
| 4,356,313 | 10/1982 | Cragoe | 560/53 |
| 4,356,314 | 10/1982 | Cragoe | 560/53 |
| 4,389,417 | 6/1983 | Bourke | 424/317 |
| 4,394,385 | 7/1983 | Cragoe | 424/285 |
| 4,463,208 | 7/1984 | Cragoe | 562/462 |
| 4,465,850 | 8/1984 | Cragoe | 560/53 |
| 4,510,322 | 4/1985 | Blaine | 514/255 |
| 4,579,869 | 4/1986 | Cragoe | 514/561 |
| 4,604,396 | 8/1986 | Cragoe | 514/256 |

FOREIGN PATENT DOCUMENTS 181100 5/1986 European Pat. Off. .

OTHER PUBLICATIONS

E. J. Cragoe, Jr., et al., "Agents For the Treatment of Brain Injury, 1. (Aryloxy)alkanoic Acids," J. Med. Chem., 25, 567–579 (1982).

E. J. Cragoe, Jr., et al., "Agents For the Treatment of Brain Edema, 2. . . . ," J. Med. Chem., 29, 825–841 (1986).

O. W. Woltersdorf, Jr., et al., "(Acylaryloxy)acetic Acid Diuretics. 1. (2-Alkyl- and 2,2-Dialkyl-1-oxo-5-indanyloxy)acetic Acids," J. Med. Chem., 20, 1400–1408 (1977).

R. S. Bourke et al., "Swelling and Ion Uptake in Cat Cerebrocortical Slices: Control by Neurotransmitters and Ion Transport Mechanisms," Neurochem. Res., 8, 5–23 (1983).

E. J. Cragoe, Jr., "Drugs For the Treatment of Traumatic Brain Injury," Medicinal Research Reviews 1, 271–305 (1987).

Primary Examiner—Alan Siegel
Attorney, Agent, or Firm—Hesna J. Pfeiffer

[57] ABSTRACT

This invention relates to novel [(2-substituted 1,2-dihydro-1-oxo-1H-inden-5-yl)oxy]alkanesulfonic acids and salts thereof. The compounds are useful for the treatment and prevention of injury to the brain and of edema due to head trauma, stroke (particularly ischemic), arrested breathing, cardiac arrest, Reye's syndrome, cerebral thrombosis, cerebral embolism, the neurological problems caused by AIDS, cerebral hemorrhage, cerebral tumors, encephalomyelitis, spinal cord injury, hydrocephalus, post-operative brain injury trauma, edema due to cerebral infections, various brain concussions, and elevated intracranial pressure.

25 Claims, No Drawings

[(2-SUBSTITUTED 1,2-DIHYDRO-1-OXO-1H-INDEN-5-YL)OXY]ALKANESULFONIC ACIDS AND SALTS THEREOF

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, the neurological problems caused by AIDS, cerebral hemorrhage, encephalomyelitis, hydrocephalus, post-operative brain injury, cerebral infections, various concussions, and elevated intracranial pressure results in edema and swelling of the affected tissues. This is followed by ischemia, hypoxia, necrosis, temporary or permanent brain or spinal cord injury and may result in death. The tissue mainly affected are classified as gray matter, more specifically astroglial cells. The specific therapy currently used for treatment of medical problems described include various kinds of diuretics (particularly osmotic diuretics), steroids (such as, 6-α-methylprednisolone succinate), and barbiturates. The usefulness of these agents is questionable and they are associated with a variety of untoward complications and side effects. See e.g., E. J. Cragoe, Jr., *Medicinal Research Reviews*, 7, 271–35 (1987). Thus, the compounds of this invention comprise a novel and specific treatment of medical problems where no specific therapy is available.

Certain (indanyloxy)alkanoic acid derivatives have been disclosed as useful agents for the treatment and prevention of injury to the brain and spinal cord. See Cragoe et al., *J. Med. Chem.*, 25, 567–579 (1982) and U.S. Pat. Nos. 4,579,869, 4,465,850, 4,463,208, 4,394,285, and 4,389,417. None of these publications, however, discloses the [(1,2-dihydro-1-oxo-1H-inden-5-yl)oxy]alkanesulfonic acids or salts of the present invention nor suggests their utility for treatment of brain injury or edema. Moreover, the U.S. Pat. No. 4,394,385 discloses indeno[5,4-b]furancarboxylic acids that have a structurally distinct ring system from the compounds of the present invention.

Certain [(tetrahydrofluoren-7-yl)oxy]alkanoic acid derivatives have also been disclosed as useful agents for the treatment and prevention of injury to the brain and spinal cord. See Cragoe et al., *J. Med. Chem.* 29, 825–841 (1986) and U.S. Pat. Nos. 4,604, 396, 4,356,314, 4,356,313, 4,337,354, 4,317,922, and 4,316,043. The compounds disclosed in these publications, however, are carboxylic acid derivatives having a fluorenyl ring nucleus and thus are structurally distinct from the [(1,2-dihydro-1-oxo-1H-inden-5-yl)oxy]alkanesulfonic acids and salts of the present invention.

The compounds of the present invention have the added advantage of being devoid of the pharmacodynamic, toxic or various side effects characteristic of the diuretics, steroids and barbiturates.

SUMMARY OF THE INVENTION

This invention relates to novel [(2-substituted-1,2-dihydro-1-oxo-1H-inden-5-yl)oxy]alkanesulfonic acids and salts thereof of Formula I that are useful in the treatment and prevention of brain injury and edema.

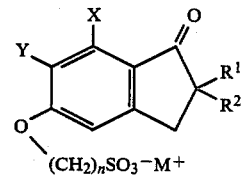

or optical isomers thereof; or a hydrate or other solvate thereof;

wherein $R^1$ is:
(a) $C_1$–$C_6$ alkyl;
(b) $C_3$–$C_7$ cycloalkyl;
(c) $C_4$–$C_{11}$ (cycloalkyl)alkyl;
(d) phenyl or phenyl substituted with one or more substituents selected from the group consisting of:
  (i) halogen;
  (ii) $C_1$–$C_6$ alkyl;
  (iii) $C_1$–$C_6$ alkoxy;
  (iv) $C_2$–$C_6$ alkanoyl; and
  (v) hydroxy; or
(e) phenyl($C_1$–$C_6$ alkyl) or phenyl($C_1$–$C_6$ alkyl) substituted in the benzene ring with one or more substituents selected from the group consisting of:
  (i) halogen;
  (ii) $C_1$–$C_6$ alkyl;
  (iii) $C_1$–$C_6$ alkoxy;
  (iv) $C_2$–$C_6$ alkanoyl; and
  (v) hydroxy;

$R^2$ is:
(a) hydrogen; or
(b) $C_1$–$C_6$ alkyl;

X and Y are independently:
(a) halogen; or
(b) $C_1$–$C_6$ alkyl;

$M^+$ is a pharmaceutically acceptable cation; and
n is an integer of from 1 to 6.

The term "$C_1$–$C_6$ alkyl" refers to straight or branched chain aliphatic hydrocarbon groups having from 1 to 6 carbon atoms, also referred to as lower alkyl. Examples of $C_1$–$C_6$ alkyl are methyl, ethyl, propyl, butyl, pentyl, hexyl, and the isomeric forms thereof.

The term "$C_3$–$C_7$ cycloalkyl" refers to saturated monocyclic hydrocarbon groups having from 3 to 7 carbon atoms in the ring. Examples of $C_3$–$C_7$ cycloalkyl are cyclopropyl, cyclobutyl, cyclopentyl, cyclohexyl, and cycloheptyl.

The term "$C_4$–$C_{11}$(cycloalkyl)alkyl" refers to straight or branched chain alkyl groups bearing a cycloalkyl group such that the total number of carbon atoms ranges from 4 to 11. Examples of $C_4$–$C_{11}$ (cycloalkyl)alkyl are cyclopropylmethyl, 2-cyclopropylethyl, 3-cyclopropylpropyl, cyclobutylmethyl, 2-cyclobutylethyl, cyclopentylmethyl, 2-cyclopentylethyl, cyclohexylmethyl, 2-cyclohexylethyl, cycloheptymethyl, 2-cycloheptylethyl, and the like, and the isomeric forms thereof.

The term "$C_1$–$C_6$ alkoxy" refers to straight or branched chain alkyl oxy groups having from 1 to 6 carbon atoms. Examples of $C_1$–$C_6$ alkoxy are methoxy, ethoxy, propoxy, butoxy, pentyloxy, hexyloxy, and the isometric forms thereof.

The term "$C_2$–$C_6$ alkanoyl" refers to straight or branched chain alkanoyl groups having from 2 to 6 carbon atoms. Examples of $C_2$–$C_6$ alkanoyl are acetyl, propanoyl, butanoyl, pentanoyl, hexanoyl, and the isomeric forms thereof.

Examples of halogen are fluorine, chlorine, bromine, and iodine.

The term "pharmaceutically acceptable cation" refers to a positively charged inorganic or organic ion that is generally considered suitable for human consumption. Examples of pharmaceutically acceptable cations are hydrogen, alkali metal (lithium, sodium, and potassium), magnesium ($\frac{1}{2}$Mg++), calcium ($\frac{1}{2}$Ca++), ammonium, alkylammonium, dialkylammonium, trialkylammonium, tetraalkylammonium, diethanolaminium, triethanolaminium, and guanidinium ions, and protonated forms of lysine, benzathine, procaine, and choline. Cations may be interchanged by methods known in the art, such as ion exchange. Where compounds of Formula I are prepared in the sulfonic acid form (that is, where M+ is hydrogen ion), addition of a base form of the cation (such as a hydroxide or a free amine) will yield the appropriate cationic form.

When the substituents $R^1$ and $R^2$ are different, the 2-position of the indanone ring system is asymmetric and the compounds of this invention of Formula I are racemic. One skilled in the art would understand that compounds of Formula I or their precursors could be resolved into enantiomeric components, which may vary somewhat as to desirable activity or toxicity. One skilled in the art could readily determine the most desirable isomeric composition. It is understood that this invention encompasses the racemic mixtures and the enantiomers.

It is also understood that the compounds of Formula I may form hydrates or other solvates from the solvents in which they are prepared or from which they are crystallized. These hydrates or other solvates may be used per se or they may be dehydrated or desolvated by heating (for example, at about 70° C. to 100° C.) in vacuo.

Although this invention primarily involves novel compounds of Formula I, it also includes derivatives such as oximes, hydrazones, and the like. Additionally, this invention includes pharmaceutical compositions in unit dosage forms containing a pharmaceutical carrier and a pharmaceutically effective amount of a compound of Formula I (as racemate or as R or S enantiomer) for treating or preventing brain injury and edema. The method of treating a person with brain injury by administering said compounds or said pharmaceutical compositions is also part of this invention.

DESCRIPTION OF THE INVENTION

The compounds of this invention may be prepared from phenolic indanones of Formula II, which can be prepared using methods known in the art. See, for example, Cragoe et al., *J. Med. Chem.*, 25, 567–579 (1982), and Woltersdorf et al., *J. Med. Chem.*, 20, 1400–1408 (1977).

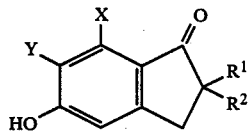

Phenolic indanones of Formula II react under suitably basic conditions in a suitable organic solvent with a suitable alkanesulfonate derivative to form compounds of this invention, Formula I, in which M+ is the cation moiety derived from the base employed. Suitably basic conditions are achieved by adding a base that can generate a sufficient phenoxide concentration for the reaction with the alkanesulfonate derivative to occur but that does not itself form significant quantities of byproducts by reaction with other chemical reagents or reaction products. Examples of such bases include alkali metal carbonates, such as lithium, sodium, or potassium carbonate; alkali metal alkoxides, such as sodium methoxide, sodium ethoxide, and potassium t-butoxide; alkali metal alkyls, such as n-butyllithium and t-butyllithium; and other such bases known in the art. In general, the base is added to a solution or suspension of a phenolic indanone of Formula II before adding the alkanesulfonate derivative. Suitable organic solvents are organic liquids in which reactants may be dissolved or suspended but which are otherwise chemically inert. Examples of suitable organic solvents include alkanols, such as methanol, ethanol, propanol, isopropyl alcohol, and the like; alkanes and cycloalkanes; ethers and cyclic ethers, such as diethyl ether, tetrahydrofuran, tetrahydropyran, and the like; aromatic hydrocarbons, such as benzene, toluene, and the like; N,N-disubstituted amides, such as dimethylformamide, dimethylacetamide, and the like; N-substituted lactams, such as N-methylpyrrolidinone, N-methylpiperidinone, and the like; and other solvents known in the art. The particular base used depends somewhat on the solvent used. For example, a preferred organic solvent is ethanol, for which the preferred base is sodium ethoxide.

Suitable alkanesulfonate derivatives are compounds of the formula L—(CH$_2$)$_n$—SO$_2$—OB, wherein L is a suitable leaving group for alkylating phenoxide oxygen atoms, and B is hydrogen or a suitable sulfonate blocking group that can later be removed. The group L can be, for example, halogen or methanesulfonate. Sulfonate blocking groups B can be, for example, alkyl or benzyl. For compounds of Formula I in which n is to be 3 or 4, L and B taken together may be a chemical bond such that the alkanesulfonate derivative is a sultone of Formula III

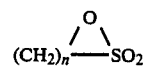

wherein n is 3 or 4. Such sultones are the preferred alkanesulfonate derivatives for preparing compounds of Formula I wherein n is 3 or 4.

Not all groups M+ to be incorporated in compounds of Formula I are cations of bases sufficiently basic to generate suitable phenoxide concentrations from phenolic indanones of Formula II. One skilled in the art could readily exchange one group M+ of Formula I for another using, for example, ion exchange. Compounds of Formula I in which M+ is hydrogen ion may also be converted to other forms by addition of a base form of the cation, such as a hydroxide or a free amine.

It is to be recognized that certain compounds of Formula I possess an asymmetric carbon atom (the 2-position of the indanone ring system) and therefore the compounds of the invention are racemates which consist of two enantiomers. These enantiomers may possess markedly different biological properties, thus it is advantageous to separate the enantiomers and use them in their pure form. The optically pure compounds of Formula I can be prepared from optically pure precursors of Formula II. Alternatively, the compounds of Formula I can be resolved to their pure enantiomers by one or more of several classical examples. For example, compounds of Formula I may be resolved by forming a salt of the racemic mixture with an optically active base such as (+) or (−)amphetamine, (−)cinchonidine, dehydroabiethylamine, (+) or (−)-α-methylbenzylamine, (+) or (−)-α-(1-naphthyl)ethylamine, (+)cinchonine, brucine, or strychnine and the like in a suitable solvent such as methanol, ethanol, isopropyl alcohol, benzene, acetonitrile, nitromethane, acetone, and the like. There is formed in the solution two diastereomeric salts one of which is usually less soluble in the solvent than the other. Repetitive recrystallization of the crystalline salt generally affords a pure diastereomeric salt from which is obtained the desired pure enantiomer. The optically pure enantiomer of the compound of Formula I is obtained by acidification of the salt with a mineral acid, isolation by filtration and recrystallization of the optically pure antipode.

The other optically pure antipode may generally be obtained by using a different base to form the diastereomeric salt. It is of advantage to isolate the partially resolved acid from the filtrates of the purification of the first diastereomeric salt and to further purify this substance through the use of another optically active base. It is especially advantageous to use an optically active base for the isolation of the second enantiomer which is the antipode of the base used for the isolation of the first enantiomer. For example, if (+)-α-methylbenzylamine was used first, then (−)-α-methylbenzylamine is used for the isolation of the second (remaining) enantiomer.

The preferred embodiments of this invention include compounds of the formula

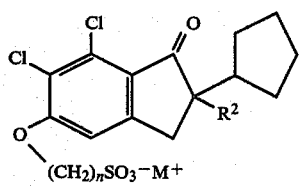

IV and optical isomers thereof; and hydrates thereof; wherein $R^2$ is $C_1$–$C_6$ alkyl, $M^+$ is an alkali metal ion, and n is 3 or 4.

More preferred embodiments of this invention include compounds of the formula

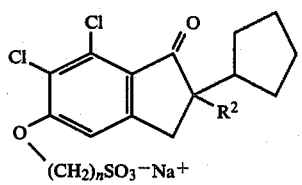

IV and optical isomers thereof; and hydrates thereof; wherein $R^1$ is straight-chain $C_1$–$C_4$ alkyl and n is 3 or 4.

Intrinsic activity in inhibiting the swelling of brain tissue was demonstrated in an in vitro cerebrocortical cat brain slice assay that simulates the edema seen in traumatic brain injury. See, e.g., Bourke et al., *Neurochem. Res.*, 8, 5 (1983), and Cragoe et al., *J. Med. Chem.*, 25, 567 (1982).

In Vitro Cerebrocortical Cat Brain Tissue Slice Assay

Adult cats of 2–3 kg body weight were employed in tissue slice studies. Prior to sacrifice, the animals were anesthetized with ketamine hydrochloride, 10 mg/kg intramuscularly. Eight (three control, five experimental) pial surface cerebrocortical tissue slices (0.5 mm thick; approximately 150 mg initial fresh weight) were cut successively with a calibrated Stadie-Riggs fresh tissue microtome without moistening and weighed successively on a torsion balance. During the slice preparation all operations except weighing were confined to a humid chamber. Each slice was rapidly placed in an individual Warburg flask containing 2 ml of incubation medium at room temperature. The basic composition of the incubation media was as follows: glucose, 10 mM; $CaCl_2$, 1.3 mM; $MgSO_4$, 1.2 mM; $KHSO_4$, 1.2 mM; HEPES (N-2-hydroxyethylpiperazine-N'-2-ethanesulfonic acid, titrated with NaOH to pH 7.4), 20 mM. Except when adding $HCO_3^-$, the osmolarity of the media was maintained isosmotic (approximately 285 mOsm/L) by reciprocal changes of $N^+$ or $K^+$ to achieve a concentration of $K^+$ of 27 mM. The basic medium was saturated with oxygen by bubbling pure oxygen through the solution for 30 minutes before use. When added, sodium bicarbonate or triethylammonium bicarbonate was initially present in the sidearm of each flask at an initial concentration of 50 mM in 0.5 ml of complete medium. Nonbicarbonate control slices were incubated at 37° C. in 2.5 ml of basic medium for 60 minutes. Bicarbonate control slices were similarly incubated for an initial 20 minutes at 37° C. in 2.0 ml of basic medium to which was added from the sidearm an additional 0.5 ml of incubation medium containing 50 mM $HCO_3^-$, which, after mixing, resulted in a $HCO_3^-$ concentration of 10 mM and a total volume of 2.5 ml. The incubation is continued for an additional 40 minutes. The various compounds could be tested as aqueous solutions of salts which are formed by reaction with appropriate bases in water. Just prior to incubation, all flasks containing $HCO_3^-$ were gassed for 5 minutes with 2.5% $CO_2$/97.5% $O_2$ instead of 100% $O_2$.

Following the 60-minute incubation period, tissue slices were separated from incubation medium by filtration, reweighed, and homogenized in 1N $HClO_4$ (10% w/v) for electrolyte analysis. The tissue content of ion is expressed in micromoles per gram initial preswelling fresh weight. Control slice swelling is expressed as microliters per gram initial preswelling fresh weight. The effectiveness of an inhibitor at a given concentration was measured by the amount of $HCO_3^-$-stimulated swelling that occurred in its presence, computed as a percent of the maximum possible and is reported as an $IC_{50}$, (See, e.g., Table I (Example 6)). Tissue and media $Na^+$ and $K^+$ levels were determined by emission flame photometry with $Li^+$ internal standard; $Cl^-$ levels were determined by amperometric titration. Tissue viability during incubation is monitored by manometry.

Inasmuch as there are a variety of symptoms and severity associated with grey matter edema, particularly when it is caused by head trauma, stroke, cerebral hemorrhage or embolism, post-operative brain surgery trauma, spinal cord injury, cerebral infections, various brain concussions, elevated intracranial pressure, arrested breathing, cardiac arrest, Reye's syndrome cerebral tumors, encephalomeylitis, hydrocephalus and neurological problem caused by AIDS, the precise treatment is left to the practioner. Generally, candidates for treatment will be indicated by the results of the patient's initial general neurological status, findings on specific clinical brain stem functions and findings on computerized axial tomography (CAT), nuclear magnetic resonance (NMR) or positron emission tomography (PET) scans of the brain. The sum of the neurological evaluation is presented in the Glasgow Coma Score or similar scoring system. Such a scoring system is often valuable in selecting the patients who are candidates for therapy of this kind.

The compounds of this invention can be administered by a variety of established methods, including intravenously, intramuscularly, subcutaneously, or orally. The parenteral route, particularly the intravenous route of administration, is preferred, especially for the very ill and comatose patient. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous administration of drugs of the type of Formula I in the form of their salts is superior.

A recommended dosage range for treatment is expected to be from 0.05 mg/kg to 50 mg/kg of body weight as a single dose, preferably from 0.5 mg/kg to 20 mg/kg. An alternative to the single dose schedule is to administer a primary loading dose followed by a sustaining dose of half to equal the primary dose, every 4 to 24 hours. When this multiple dose schedule is used the dosage range may be higher than that of the single dose method. Another alternative is to administer an ascending dose sequence of an initial dose followed by a sustaining dose of 1½ to 2 times the initial dose every 4 to 24 hours. For example, three intravenous doses of 4, 8, 12, or 16 mg/kg of body weight can be given at 6 hour intervals. If necessary, four additional doses of 4, 8, 12, or 16 mg/kg of body weight can be given at 12 hour intervals. Another effective dose regimen consists of a continuous intravenous infusion of from 0.05 mg/kg/hr to 3.0 mg/kg/hr. Of course, other dosing schedules and amounts are possible.

One aspect of this invention is the treatment of persons with grey matter edema by concomitant administration of a compound of Formula I and an antiinflammatory steroid. These steroids are of some, albeit limited, use in control of white matter edema associated with ischemic stroke and head injury. Steroid therapy is given according to established practice as a supplement to the compound of Formula I. Similarly, a barbiturate may be administered as a supplement to treatment with a compound of Formula I.

The compounds of this invention are utilized by formulating a pharmaceutically effective amount of at least one compound of Formula I in a pharmaceutical composition such as tablet, capsule, or elixir for oral administration. Sterile solutions or suspensions can be used for parenteral administration. A compound or mixture of compounds of Formula I is compounded with a non-toxic pharmaceutically acceptable vehicle, carrier, excipient, binder, preservative, stabilizer, flavor, and the like, in a dosage form as called for by accepted pharmaceutical practice.

Illustrative of the adjuvants which may be incorporated in tablets, capsules, and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar, or the like. A syrup or elixir may contain the active compound, sucrose as a sweetening agent, methyl and propyl parabens as preservatives, a dye, and a flavoring such as cherry or orange flavor.

Sterile compositions for injection or infusion can be formulated according to conventional pharmaceutical practice by dissolving the active substance in a conventional vehicle such as water, saline, or dextrose solution by forming a soluble salt in water using an appropriate acid, such as a pharmaceutically acceptable carboxylic acids or mineral acids. Alternatively, a suspension of the active substance in a naturally occurring vegetable oil like sesame oil, coconut oil, peanut oil, cottonseed oil, and the like, or a synthetic fatty vehicle like ethyl oleate or the like may be formulated for injection or infusion. Buffer, preservatives, antioxidants, and the like can be incorporated as required.

The following Examples are included to illustrate the preparation of representative compounds of Formula I. It is intended that the specification and examples be considered as exemplary only, with the true scope and spirit of the invention being indicated by the following claims. All temperatures in the examples are in Celsius unless otherwise indicated.

DESCRIPTION OF THE PREFERRED EMBODIMENTS

EXAMPLE 1

Sodium 3-[(6,7-dichloro-2-cyclopentyl-2-methyl-1-oxo-2,3-dihydro-1H-inden-5-yl)oxy]propanesulfonate hydrate

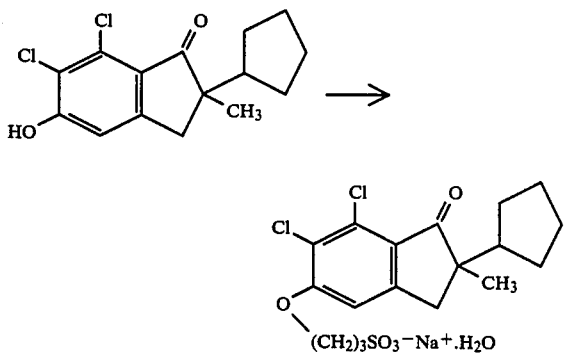

Sodium metal (1.25 g, 54.2 mmole) was added to ethanol (80 ml) and the resultant solution of sodium ethoxide was cooled to room temperature. To this solution was added with stirring 6,7-dichloro-2-cyclopentyl-5-hydroxy-2-methyl-2,3-dihydro-1H-inden-1-one (16.22 g, 54.2 mmole), followed after five minutes by 1,3-propanesultone (6.61 g, 54.1 mmole). After 20 minutes stirring, the mixture was slowly heated to reflux and then maintained at reflux overnight. After the mixture was cooled, a precipitate was collected and washed with ethanol. The solid was suspended in a mixture of ethanol (75 ml), diethyl ether (75 ml), and acetic acid (3 ml), and stirred at room temperature for three days. This solid was collected and recrystallized from water (ca. 100 ml). The precipitate was washed with water in small portions and dried overnight in a vacuum oven at about 65° to yield the title compound as the hydrate (14 g). Structure assignment was supported by the nmr spectrum and by elemental analysis.

Analysis. Calc'd for $C_{18}H_{21}Cl_2O_5SNa \cdot H_2O$: C, 46.85; H, 5.03; S, 6.95; Cl, 15.37. Found: C, 47.07; H, 4.96; S, 6.84; Cl, 15.18.

EXAMPLE 2

Sodium (+)3-[(6,7-dichloro-2-cyclopentyl-2-methyl-1-oxo-2,3-dihydro-1H-inden-5-yl)oxy]propanesulfonate hydrate

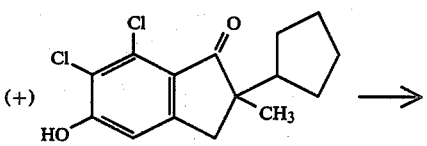

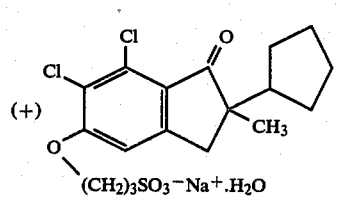

Sodium ethoxide was prepared as in Example 1 using 0.262 g (11.4 mole) of sodium metal and 35 ml of ethanol. To the ethoxide solution was added (+)6,7-dichloro-2-cyclopentyl-5-hydroxy-2-methyl-2,3-dihydro-1H-inden-1-one (3.406 g, 11.4 mmole), followed by 1,3-propanesultone (1.390 g, 11.4 mmole). The mixture was heated to reflux, diluted with ethanol (15 ml) to improve stirring, and further heated at 90° for six hours. The slurry was diluted with ethanol (50 ml), diethyl ether (75 ml), and acetic acid (2 ml), and stirred vigorously for one hour. The solid was collected, washed with 1:1 ethanol-diethyl ether, dried partially under vacuum, and then recrystallized from water (30 ml). The precipitate was collected, washed with small portions of water, and dried at 100° over phosphorus pentoxide to yield the title compound as the hydrate (2.9 g), m.p. ca. 277°. Structure assignment was supported by the nmr spectrum and by elemental analysis.

Analysis. Calc'd for $C_{18}H_{21}Cl_2O_5SNa \cdot H_2O$: C, 46.85; H, 5.03. Found: C, 47.20; H, 4.94.

EXAMPLE 3

Sodium (+)4-[(6,7-dichloro-2-cyclopentyl-2-methyl-1-oxo-2,3-dihydro-1H-inden-5-yl)oxy]butanesulfonate hydrate

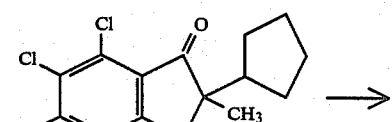

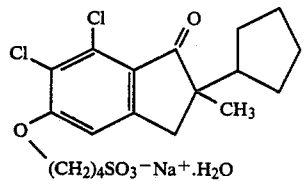

The title compound is prepared by the method of Example 2 using 1,4-butanesultone instead of 1,3-propanesultone.

EXAMPLE 4

Sodium 3-[(6,7-dichloro-2-cyclopentyl-2-ethyl-1-oxo-2,3-dihydro-1H-inden-5-yl)oxy]propanesulfonate hydrate

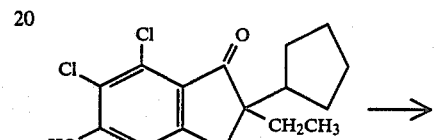

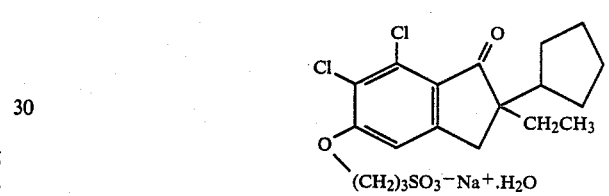

The title compound is prepared by the method of Example 1 using 6,7-dichloro-2-cyclopentyl-5-hydroxy-2-ethyl-2,3-dihydro-1H-inden-1-one instead of 6,7-dichloro-2-cyclopentyl-5-hydroxy-2-methyl-2,3-dihydro-1H-inden-1-one.

EXAMPLE 5

Sodium 3-[(3-butyl-6,7-dichloro-2-cyclopentyl-1-oxo-2,3-dihydro-1H-inden-5-yl)oxy]propanesulfonate hydrate

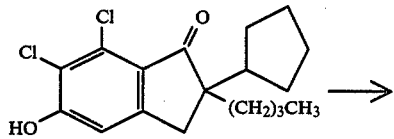

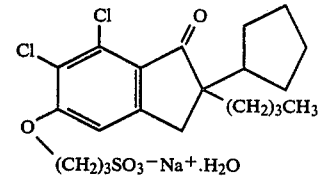

The title compound is prepared by the method of Example 1 using 2-butyl-6,7-dichloro-2-cyclopentyl-1-oxo-2,3-dihydro-1H-inden-1-one instead of 6,7-dichloro-2-cyclopentyl-5-hydroxy-2-methyl-2,3-dihydro-1H-inden-1-one.

EXAMPLE 6

Biological results

TABLE I
In vitro Cerebrocortical Cat Brain Tissue Slice Assay

| Compound (Example No.) | IC$_{50}$ (nM) |
|---|---|
| 1 | 20 |
| 2 | 20 |

What is claimed is:

1. A compound having the formula:

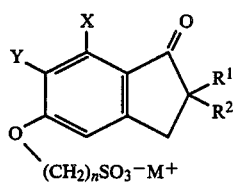

or optical isomers thereof; or a hydrate or other solvate thereof;
wherein R$^1$ is:
  (a) C$_1$–C$_6$ alkyl;
  (b) C$_3$–C$_7$ cycloalkyl;
  (c) C$_4$–C$_{11}$(cycloalkyl)alkyl;
  (d) phenyl or phenyl substituted with one or more substituent selected from the group consisting of:
    (i) halogen;
    (ii) C$_1$–C$_6$ alkyl;
    (iii) C$_2$–C$_6$ alkoxy;
    (iv) C$_2$–C$_6$ alkanoyl; and
    (v) hydroxy; or
  (e) phenyl(C$_1$–C$_6$ alkyl) or phenyl(C$_1$–C$_6$ alkyl) substituted in the benzene ring with one or more substituents selected from the group consisting of:
    (i) halogen;
    (ii) C$_1$–C$_6$ alkyl;
    (iii) C$_2$–C$_6$ alkoxy;
    (iv) C$_2$–C$_6$ alkanoyl; and
    (v) hydroxy;
R$^2$ is:
  (a) hydrogen; or
  (b) C$_1$–C$_6$ alkyl;
X and Y are independently:
  (a) halogen; or
  (b) C$_1$–C$_6$ alkyl;
M$^+$ is a pharmaceutically acceptable cation; and
n is an integer of from 1 to 6.

2. A compound according to claim 1 wherein X and Y are independently halogen.

3. A compound according to claim 2 wherein the halogen is chlorine.

4. A compound according to claim 1 wherein R$^1$ is C$_3$–C$_7$ cycloalkyl.

5. A compound according to claim 4 wherein R$^1$ is cyclopentyl.

6. A compound according to claim 1 having the formula

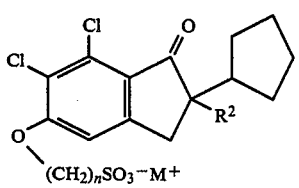

or optical isomers thereof;
or a hydrate or other solvate thereof; wherein
  R$^2$ is hydrogen or C$_1$–C$_6$ alkyl;
  M$^+$ is a pharmaceutically acceptable cation; and
  n is an integer of from 1 to 6.

7. A compound according to claim 6 wherein R$^2$ is C$_1$–C$_6$ alkyl.

8. A compound according to claim 6 wherein the pharmaceutically acceptable cation is an alkali metal ion.

9. A compound according to claim 6 wherein n is 3 or 4.

10. A compound according to claim 6 wherein the hydrate or other solvate thereof is a hydrate.

11. A compound according to claim 6 having the formula

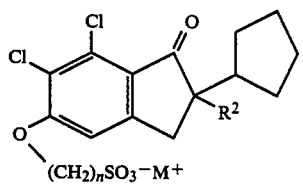

or optical isomers thereof;
or a hydrate thereof; wherein
  R$^2$ is C$_1$–C$_6$ alkyl;
  M$^+$ is an alkali metal ion; and
  n is 3 or 4.

12. A compound according to claim 11 wherein R$^2$ is C$_1$–C$_4$ alkyl.

13. A compound according to claim 11 wherein the alkali metal ion is sodium.

14. A compound according to claim 11 having the formula

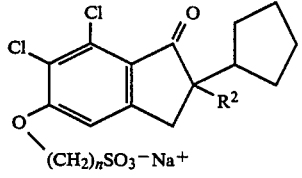

or optical isomers thereof;
or a hydrate thereof;
wherein R$^2$ is C$_1$–C$_6$ alkyl and n is 3 or 4.

15. A compound according to claim 14 which is sodium 3-[(6,7-dichloro-2-cyclopentyl-2-methyl-1-oxo-2,3-dihydro-1H-inden-5-yl)oxy]propanesulfonate or a hydrate thereof.

16. A compound according to claim 14 which is sodium (+)3-[(6,7-dichloro-2-cyclopentyl-2-methyl-1-oxo-2,3-dihydro-1H-inden-5-yl)oxy]propanesulfonate or a hydrate thereof.

17. A compound according to claim 14 which is sodium (+)4-[(6,7-dichloro-2-cyclopentyl-2-methyl-1-oxo-2,3-dihydro-1H-inden-5-yl)oxy]butanesulfonate or a hydrate thereof.

18. A compound according to claim 14 which is sodium 3-[(6,7-dichloro-2-cyclopentyl-2-ethyl-1-oxo-2,3-dihydro-1H-inden-5-yl)oxy]propanesulfonate or a hydrate thereof.

19. A compound according to claim 14 which is sodium 3-[(2-butyl-6,7-dichloro-2-cyclopentyl-1-oxo-2,3- dihydro-1H-inden-5-yl)oxy]propanesulfonate or a hydrate thereof.

20. A pharmaceutical composition useful in the treatment of brain injury and edema comprising a pharmaceutically effective amount of at least one compound according to claim 1, together with one or more non-toxic pharmaceutically acceptable carriers.

21. A pharmaceutical composition according to claim 20 wherein said compound is selected from the group consisting of:
- sodium 3-[(6,7-dichloro-2-cyclopentyl-2-methyl-1-oxo-2,3-dihydro-1H-inden-5-yl)oxy]propanesulfonate;
- sodium (+)3-[(6,7-dichloro-2-cyclopentyl-2-methyl-1-oxo-2,3-dihydro-1H-inden-5-yl)oxy]propanesulfonate;
- sodium (+)4-[(6,7-dichloro-2-cyclopentyl-2-methyl-1-oxo-2,3-dihydro-1H-inden-5-yl)oxy]butanesulfonate;
- sodium 3-[(6,7-dichloro-2-cyclopentyl-2-ethyl-1-oxo-2,3-dihydro-1H-inden-5-yl)oxy]propanesulfonate; and
- sodium 3-[(2-butyl-6,7-dichloro-2-cyclopentyl-1-oxo-2,3-dihydro-1H-inden-5-yl)oxy]propanesulfonate.

22. A method for treating brain injury and edema comprising administering a pharmaceutically effective amount of at least one compound of claim 1 to a patient in need of such treatment.

23. A method according to claim 22 wherein said compound is selected from the group consisting of:
- sodium 3-[(6,7-dichloro-2-cyclopentyl-2-methyl-1-oxo-2,3-dihydro-1H-inden-5-yl)oxy]propanesulfonate;
- sodium (+)3-[(6,7-dichloro-2-cyclopentyl-2-methyl-1-oxo-2,3-dihydro-1H-inden-5-yl)oxy]propanesulfonate;
- sodium (+)4-[(6,7-dichloro-2-cyclopentyl-2-methyl-1-oxo-2,3-dihydro-1H-inden-5-yl)oxy]butanesulfonated;
- sodium 3-[(6,7-dichloro-2-cyclopentyl-2-ethyl-1-oxo-2,3-dihydro-1H-inden-5-yl)oxy]propanesulfonate; and
- sodium 3-[(2-butyl-6,7-dichloro-2-cyclopentyl-1-oxo-2,3-dihydro-1H-inden-5-yl)oxy]propanesulfonate.

24. A method for treating brain injury and edema comprising administering a pharmaceutically effective amount of a pharmaceutical composition of claim 20 to a patient in need of such treatment.

25. A method according to claim 24 wherein the compound of said pharmaceutical composition is selected from the group consisting of:
- sodium 3-[(6,7-dichloro-2-cyclopentyl-2-methyl-1-oxo-2,3-dihydro-1H-inden-5-yl)oxy]propanesulfonate;
- sodium (+)3-[(6,7-dichloro-2-cyclopentyl-2-methyl-1-oxo-2,3-dihydro-1H-inden-5-yl)oxy]propanesulfonate;
- sodium (+)4-[(6,7-dichloro-2-cyclopentyl-2-methyl-1-oxo-2,3-dihydro-1H-inden-5-yl)oxy]butanesulfonate;
- sodium 3-[(6,7-dichloro-2-cyclopentyl-2-ethyl-1-oxo-2,3-dihydro-1H-inden-5-yl)oxy]propanesulfonate; and
- sodium 3-[(2-butyl-6,7-dichloro-2-cyclopentyl-1-oxo-2,3-dihydro-1H-inden-5-yl)oxy]propanesulfonate.

* * * * *